United States Patent [19]

Rifu et al.

[11] Patent Number: 4,807,267
[45] Date of Patent: Feb. 21, 1989

[54] X-RAY COMPUTED TOMOGRAPHY APPARATUS

[75] Inventors: Toshihiro Rifu; Kyojiro Nambu, both of Tochigi, Japan

[73] Assignee: Kabushiki Kaisha Toshiba, Kawasaki, Japan

[21] Appl. No.: 45,467

[22] Filed: May 4, 1987

[30] Foreign Application Priority Data

May 7, 1986 [JP] Japan .................. 61-105154

[51] Int. Cl.$^4$ .................. G01T 1/20; G21F 5/04
[52] U.S. Cl. .................. 378/7; 378/901; 378/19
[58] Field of Search .................. 378/7, 4, 19, 86, 154, 378/901, 99; 358/111

[56] References Cited

U.S. PATENT DOCUMENTS

| | | | |
|---|---|---|---|
| 4,286,156 | 8/1981 | Wagner | 378/7 |
| 4,653,080 | 3/1987 | Kikuchi | 378/86 |
| 4,688,242 | 8/1987 | Ema | 378/7 |

*Primary Examiner*—Carolyn E. Fields
*Assistant Examiner*—Joseph A. Hynds
*Attorney, Agent, or Firm*—Finnegan, Henderson, Farabow, Garrett, & Dunner

[57] ABSTRACT

An X-ray computed tomography apparatus is disclosed which includes an X-ray source for irradiating an X-ray, a main detector section for detecting the X-ray passed through a subject and a scattering ray detector for detecting its scattered component. An X-ray shield member is detachably mounted between the X-ray source and the main detector section to shield the main X-ray. The apparatus thus manufactured evaluates a ratio between an amount of scattered component incident on the main detector section when the main X-ray is shielded from the X-ray shield member and an amount of scattered component which is detected by the scattering ray detector. With this ratio placed as K, an amount of X-ray, m, to be measured is found from $$m = b - a/K$$

where a denotes the scattered component detected by the scattering ray detector and b denotes an output level of the main detector section when the X-ray is not shielded. In this connection it is to be noted that, with this ratio K placed as such, the values b, a are generally given without any X-ray shield member.

10 Claims, 5 Drawing Sheets

X-RAY COMPUTED TOMOGRAPHY APPARATUS

BACKGROUND OF THE INVENTION

This invention relates to an X-ray CT (computed tomography) apparatus.

In general, an X-ray CT apparatus includes a main detector for detecting an X-ray and its scattered components transmitted through a subject after that X-ray has been emitted from an X-ray source and out-of-plane detectors (OOPS) for detecting scattered components corresponding to the scattered components which have been incident onto the main detector. In this case, accurate X-ray data is evaluated by subtracting the data of the scattered components which have been detected by the OOPS from the detection level of the main detector.

According to the aforementioned method, when the scattered components transmitted through the same subject are incident to the main detector and the OOPS, the measured value a detected by the OOPS and measured value b detected by the main detector are such that the greater part of the measured value b shows an amount of X-ray, m, of a main ray, i.e., a ray directly reaching the main detector after it has been emitted from the X-ray source and transmitted through the subject. In this case, the value $e = (b - m)$ obtained through the subtraction of the amount, m, from the measured value b represents the scattered component. In general, it does not follow that $a = e$ due to the difference, for example, in sensitivity and shape of X-ray detector. It is therefore not always possible to obtain exact X-ray data on the conventional apparatus.

SUMMARY OF THE INVENTION

It is accordingly the object of this invention to provide an X-ray computed tomography apparatus which can exactly detect the scattered component of an X-ray and obtain exact X-ray data from this amount of scattered component and an amount of X-ray detected by a main detector section.

In the obtainment of exact X-ray data, the ratio $(K = a/e)$ between the measured value a of the OOPS and the scattered component e is assumed constant and, with the prior knowledge of this ratio K, an amount of X-ray, m, can be estimated from the following expression:

$$m = b - a/k$$

According to this invention an X-ray shield member is detachably mounted between an X-ray source and a main detector to shield a main X-ray. The ratio between an amount of scattered component, a, falling on the main detector when the main X-ray is shielded by the X-ray shield member, and an amount of scattered component, e, which is detected by a scattering ray detector, is calculated.

DETAILED EXPLANATION OF THE PREFERRED EMBODIMENT

Figure 1:
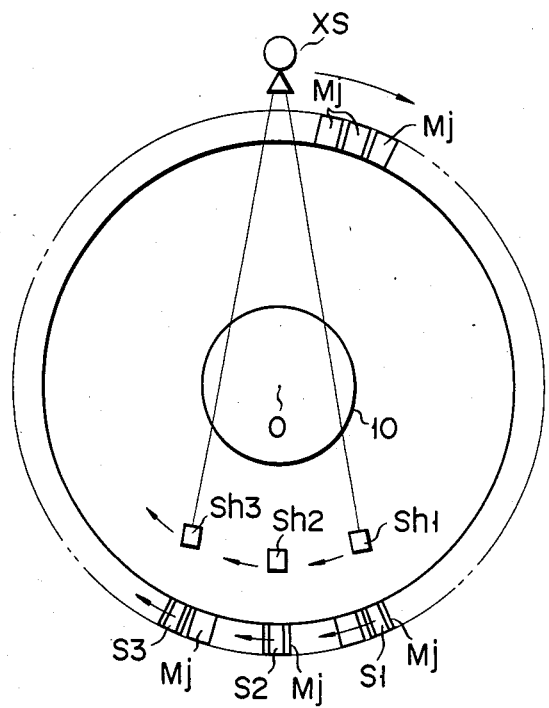
FIG. 1 is a diagrammatic view showing an X-ray computed tomography (CT) apparatus according to one embodiment of this invention.
Figure 2:
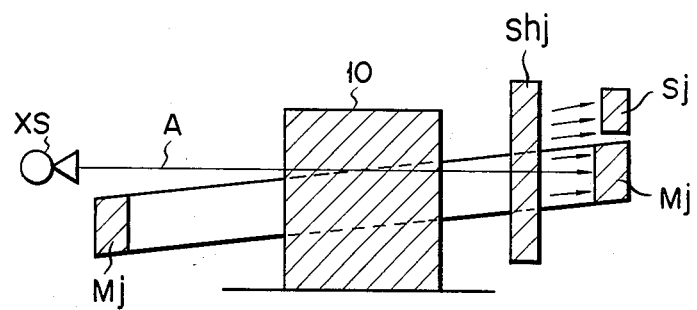
FIG. 2 is a side view showing the X-ray CT apparatus of FIG. 1.
Figure 3:
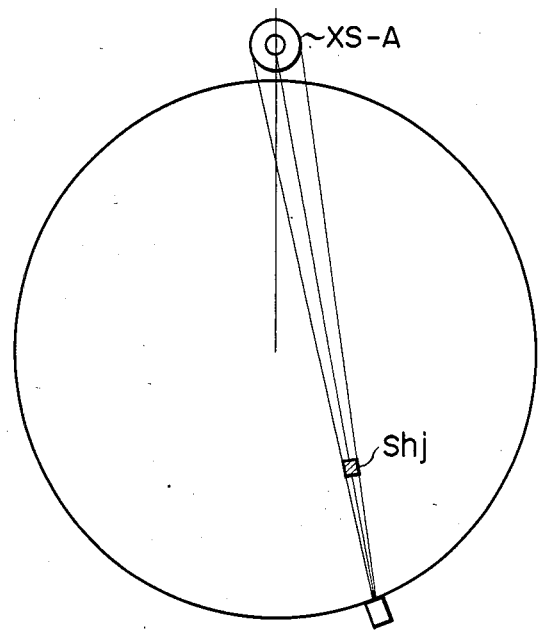
FIG. 3 is a view showing a positional relationship among an X-ray tube, shield member and main detector.

FIG. 1 shows an embodiment of this invention as applied to an X-ray CT apparatus of a fourth generation. According to this CT apparatus, a larger number of main detectors Mj (j=1~m) are fixedly arranged in a circular array with an X-ray source XS rotatable along the circumference of the circular array of these detectors Mj. Out-of-plane detectors (OOPS) Sj (j=1 to 3) are arranged opposite to the X-ray source XS such that they can be rotated together with the X-ray source XS. Out-of-plane detector Sj is arranged in close proximity over the main detector Mj so that the surface of main detector Mj coincides with that of out-of-plane detector Si, as shown in FIG. 2. X-ray shield members Shj (j=1 to 3) are detachably mounted between detector Sj and X-ray source XS. X-ray shield member Shj is comprised of a lead prism of 7 to 6 mm in thickness and located 50 to 150 mm apart from the main detector Mj in a direction perpendicular to a slice plane A. X-ray shield member Shj is of sufficient size to allow a rotary anode XS-A never to be seen from the main detector Mj side, that is, Shj has a sufficient length so as to cover main detector Mj and preferably out-o-plane detector Sj. Although in this embodiment, X-ray shield member Shj is located in proximity to the scattering ray detector, it may be positioned on the side of the X-ray source.

Subject 10 is placed, as a reference scattering object, at the center 0 of the circumference of the circular array, as set forth above, in which case the center axis of subject 10 is located in alignment with the center of the circular array and the center axis of the scanner, i.e., the center axis of the radiation of the X-ray source XS. Subject 10 is comprised of the reference scattering object, for example, a 350 $\phi$ acrylic cylindrical body filled with water.

Figure 4:
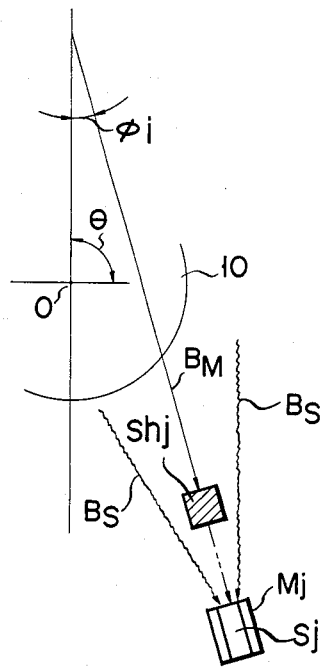
FIG. 4 is a view showing a shielded main X-ray and the state in which scattered rays fall on a main detector on the apparatus of FIG. 1.
Figure 5:
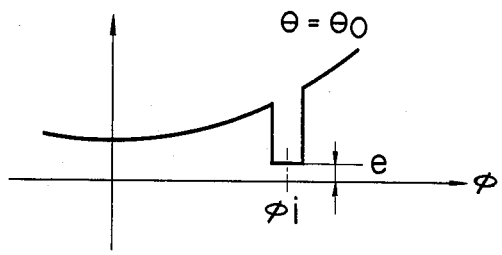
FIG. 5 is a view showing the output level of the main detector.
Figure 6:
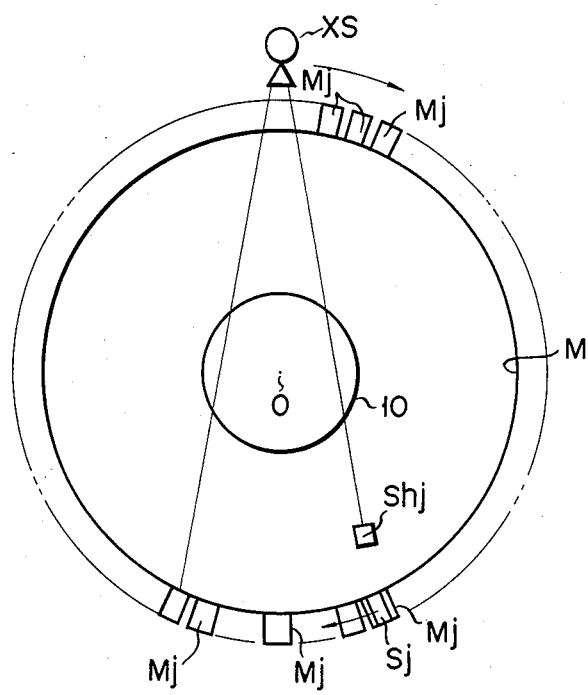
FIG. 6 is a schematic view showing an X-ray CT apparatus according to another embodiment of this invention with a shield member fixed.

When scanning is to be effected by the apparatus as shown in FIGS. 1 and 2, the X-ray source XS, together with out-of-plane detectors Sj and shield member Shj, is rotated with the scanning center axis as a rotation axis. At this time, out-of-plane detectors Sj are moved along the rotation direction to sequentially pass over different main detectors Mj. During the movement, the X-ray source XS sequentially emits X-rays. During the portions of the rotation, a main X-ray $B_M$ from the X-ray source XS is completely shielded by the shield member Shj, in a momentary fashion, as shown in FIG. 4 and is never incident onto the main detector Mj. Thus the main detector Mj receives only the X-ray components $B_S$ scattered by reference scattering object and then emerging from the direction in which they are not shielded by the shield member Shj. For this reason the output b of the main detector Mj contains the scattered component e alone, never containing any main X-ray component, i.e., represented by m=0. This value is represented by $S'_{Mj}$, where the suffix M denotes the main detector and the suffix j denotes the channel of the out-of-plane detector. The state of this output b is as shown i FIG. 5. That is, the level of the output b on a line drawn at an angle $\phi i$ to a center axis 0 is regarded as the scattered component e alone. The other out-of-plane detectors S2 and S3 detect only the corresponding scattered components for the corresponding main detectors Mj, as in the case of the detector S1, and generate the corresponding output e. In general, this value is represented by $S'_{Sj}$, where the suffix S denotes the out-of-plane detector and the suffix j denotes the channel of the out-of-plane detector.

A ratio K′ between the scattered component $S'_{Sj}$, detected by out-of-plane detector Sj and the scattered component $S'_M$ detected by the respective main detector Mj corresponding to the scattering ray detector is evaluated as follows:

$$K'j = S'_{Mj}/S_{Sj}$$

The ratio K′ is sequentially found until the X-ray source makes one rotation. The respective ratio K′j reveals a substantially constant value, depending upon a variation in the sensitivity of the scattering ray detector, a difference in position between the main detector and the out-of-plane detector, and so on, and can be regarded as being K for a whole apparatus. If, therefore, the detection output corresponding to the X-ray detected by the main detector Mj in the state not shielded by the shield member Shj is corrected by the ratio K, it is possible to obtain a detection signal corresponding to the main X-ray, i.e., X-ray data free from any scattered component.

Figure 7:
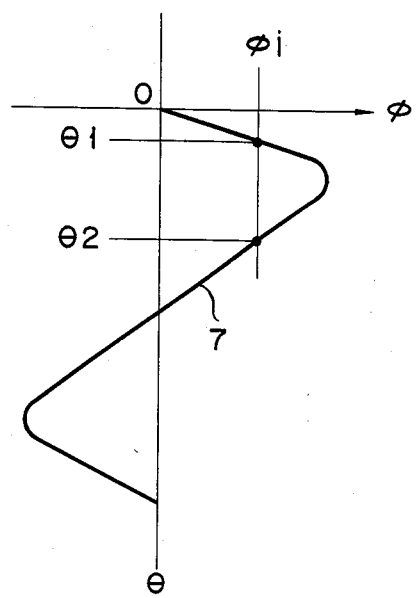
FIG. 7 is a graph showing a path of an X-ray shielded by a fixed shield member in the embodiment of FIG. 6.

Although in the aforementioned embodiment, shield member Shj, together with X-ray source XS, has been explained as being rotated as one unit, the shield member may be mounted within the main detector. In this case, the detection signal obtained from main detector section M with the rotation of the out-of-plane detector S is output as a curve signal as shown in FIG. 7 and, when shield member Shj is situated on a straight line connecting the X-ray source XS and out-of-plane detector, a signal obtained from main detector Mj at which the main X-ray is shielded by shield member Shj becomes scattered components as distinct from the main X-ray component. The rotation angle $\theta$ of the X-rays source XS corresponding to that detection position are $\theta 1$ and $\theta 2$ and K is evaluated from scattered component signal $S_M$ from main detector Mj and scattered component $S_S$ from the out-of-plane detector.

If the apparatus is of such a type that the shield member is fixed, the CT apparatus is simple in construction and in operation because there is no need to provide any mechanism for rotating the shield member.

Figure 8:
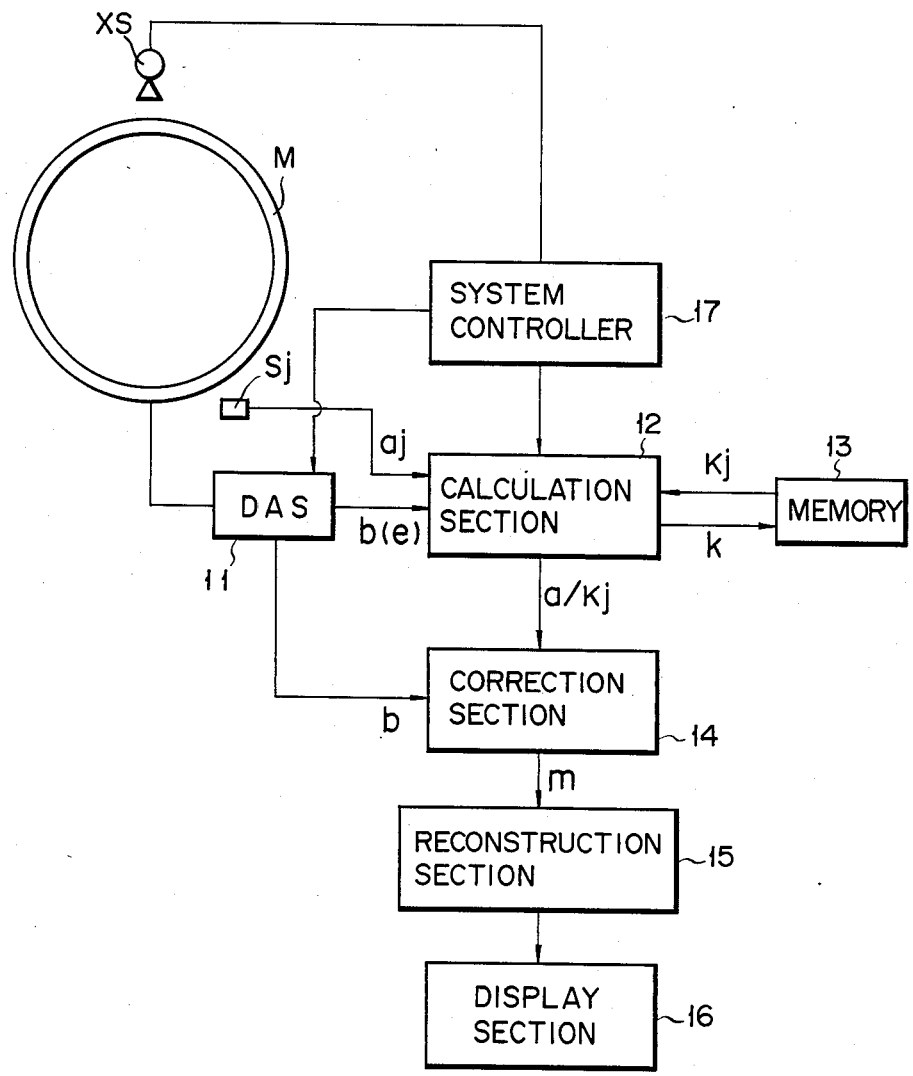
FIG. 8 is a block diagram showing the X-ray CT apparatus of this invention.

The method for evaluating K will be explained in connection with FIG. 8.

Reference scattering body 10 and shield member Shj are arranged within the main detection section (scanner) M as shown, for example, in FIG. 1. The X-ray source XS irradiates an X-ray into the subject under the control of system controller 17. In this way, a scanning operation is started on the scanner. Scanner M delivers X-ray detection data from respective main detector Mj to data collection section 11. Data collection 11 is controlled by system controller 17 and collects the X-ray detection data from CT scanner M and delivers collection data b to calculation section 12 and correction section 14. Calculation section 12 is controlled by system controller 17 and calculates Kj (=a/e) from the scattered component e of data output from data collection section 11 and scattered component a obtained from out-of-plane detector S. The result K of calculation is supplied to memory 13, where it is stored.

The operation of the X-ray CT apparatus will be explained below in connection with the process of subjecting the CT data to a scattering ray correction with the use of the value K thus obtained.

After the shield member Shj has been removed relative to the scanner, the subject is scanned, at which time the data b obtained from data collection section 11—the data detected by the main detector Mj—is supplied to correction section 14. Correction section 14 calculates aj/kj from Kj stored in memory 13 and an output aj of the detector Sj. That is, the scattered component is eliminated from the detection data b and it is, therefore, possible to evaluate the detection data m to be measured.

The data m output from correction section 14 is input to reconstituting section 15 where it is converted to CT data. The output data of reconstituting section 15 is input to display section 16 where it is displayed as a tomogram. The tomogram thus obtained is an image free from the aforementioned scattered component and is displayed as a fairly accurate image to allow diagnosis to be made in a positive way.

Figure 9:
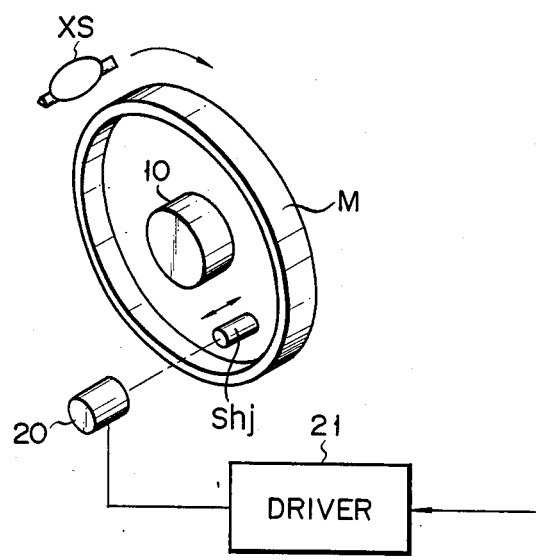
FIG. 9 is a schematic view showing a shield member automatically insertible and removable relative to the X-ray CT apparatus.

In the aforementioned embodiment, the X-ray shield member Shj is attached to an apparatus which is of such a type to permit it to be automatically inserted into, and removed from, the main detector section M. As shown in FIG. 9, for example, the shield member Shj is connected to piston 20 so that it is inserted into, or removed from, the main detector section M when the piston is driven by driver 21, which is actuated responsive to an operation signal. In this case, correction data a and K are readily obtained by automatically inserting and removing the shield member Shj into and from the main detection section M.

According to this invention, it is not necessary to evaluate the aforementioned correction data each time the subject (the patient) is to be examined. The correction of the input data can be precisely implemented by reading from the memory the correction data which has been obtained as set forth above.

As the shield member, use may be made of not only lead, but also molybdenum or tungsten.

What is claimed is:

1. An X-ray computed tomography apparatus comprising:
    X-ray irradiating means for irradiating X-rays onto a subject;
    main detection means including a plurality of X-ray detectors for detecting the X-rays passing through the subject after it has been irradiating means;
    a scattering ray detector located in a position corresponding to at least one of the X-ray detectors in said main detection means;
    main X-ray shielding means detachably insertable along a line connecting the X-ray irradiating means to said main detection means and having a dimension so as to completely shield said main detection means and said scattering ray detector from the main X-rays irradiated from said X-ray irradiation means;

means for calculating a correction coefficient from a first and second scattered-component detection data which are respectively output from said main detection means and said scattering ray detector, which detect scattered components caused due to a reference scattering body located in place of said subject with the main X-ray shielding means being inserted between said X-ray irradiating means and a group of said X-ray detectors of said main detection means and said scattering ray detector to shield both said main detection means and said scattering ray detector from said main X-ray emitted from said X-ray irradiating means, said correction coefficient being calculated from a ratio between said first and second scattered-component detection data; and means for correcting X-ray information corresponding to the X-rays, having been passed through the subject and detected by said main detection means, with the use of said correction coefficient obtained by said calculating means and a scattering ray value detected by said scattering ray detector and estimated as a detection value detected by said main detection means, wherein said X-ray information is calculated by subtracting the scattering ray value divided by the correction coefficient from a value obtained as an output of said main detection means without said main X-ray shielding means being inserted.

2. An X-ray computed tomography apparatus according to claim 1, wherein said main detection means is comprised of a circular array of main detectors, said X-ray irradiating means is comprised of an X-ray source rotating along the outer periphery of said main detection means, and said scattering ray detector and said main X-ray shielding means are means which, together with said X-ray source, rotate as one unit.

3. An X-ray computed tomography apparatus according to claim 3, wherein said shield member is made of a material selected from the group consisting of lead, tungsten and molybdenum.

4. An X-ray computed tomography apparatus according to claim 1, wherein said main detection means is comprised of a circular array of main detectors, said X-ray irradiating means is comprised of an X-ray source rotating along an outer periphery of said main detection means, said main X-ray shielding means has an X-ray shielding member fixedly arranged at a predetermined location of said main detection means, and said scattering ray detector is comprised of means which, together with said X-ray source, rotates as one unit.

5. An X-ray computed tomography apparatus according to claim 4, wherein said shielding member is made of a material selected from the group consisting of lead, tungsten and molybdenum.

6. An X-ray computed tomography apparatus according to claim 1, wherein said reference scattering body is formed of an acrylic cylinder filled with water or said reference scattering body is formed of metal or resin.

7. An X-ray computed tomography apparatus according to claim 1, wherein said main X-ray shielding means includes an X-ray shield member detachably insertible and located 50 to 150 mm away from said main detection means.

8. An X-ray computed tomography apparatus according to claim 1, wherein said X-ray shielding means is comprised of a shield member for shielding the X-rays and automatically detachable means for detachably inserting the shield member into said main detection means.

9. An X-ray computed tomography apparatus according to claim 1, wherein said scattering ray detector is comprised of an array of scattering ray detectors which, together with said X-ray irradiating means, is moved as one unit and said X-ray shielding means has a plurality of shield members which are located on a plurality of lines each connecting the X-ray irradiating means to the scattering ray detector and which, together with said scattering ray detector and said X-ray irradiating means, rotate as one unit.

10. An X-ray computed tomography apparatus according to claim 9, wherein said main detection means is comprised of a circular array of main detectors, said X-ray irradiating means is an X-ray source rotating along an outer periphery of said main detection means, and said scattering ray detector and said main X-ray shielding means are formed of means which, together with said X-ray source, rotate as one unit.

* * * * *

UNITED STATES PATENT AND TRADEMARK OFFICE
CERTIFICATE OF CORRECTION

PATENT NO. : 4,807,267
DATED : February 21, 1989
INVENTOR(S) : TOSHIHIRO RIFU ET AL.

It is certified that error appears in the above-identified patent and that said Letters Patent is hereby corrected as shown below:

In the Claims,

Claim 1, column 4, line 59, after "been" insert --irradiated by said X-ray--.

Claim 1, column 5, line 14, change "X-ray" to --X-rays--.

Claim 3, column 5, line 41, change "3" to --1--.

Claim 3, column 5, line 41, change "shield member" to --main X-ray shielding means--.

Signed and Sealed this

Seventeenth Day of April, 1990

Attest:

HARRY F. MANBECK, JR.

*Attesting Officer*    *Commissioner of Patents and Trademarks*